US009161732B2

(12) United States Patent
Takayama

(10) Patent No.: US 9,161,732 B2
(45) Date of Patent: Oct. 20, 2015

(54) RADIOGRAPHIC APPARATUS, CONTROL METHOD, AND COMPUTER PROGRAM PRODUCT

(75) Inventor: Takuzo Takayama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 388 days.

(21) Appl. No.: 13/152,758

(22) Filed: Jun. 3, 2011

(65) Prior Publication Data

US 2011/0299655 A1    Dec. 8, 2011

(30) Foreign Application Priority Data

Jun. 4, 2010  (JP) ................................. 2010-128914

(51) Int. Cl.
*G01N 23/04* (2006.01)
*A61B 6/00* (2006.01)
*A61B 6/03* (2006.01)

(52) U.S. Cl.
CPC ............... *A61B 6/4417* (2013.01); *A61B 6/032* (2013.01); *A61B 6/037* (2013.01); *A61B 6/547* (2013.01); *A61B 6/58* (2013.01)

(58) Field of Classification Search
USPC .................................................. 250/363.09
See application file for complete search history.

(56) References Cited

U.S. PATENT DOCUMENTS

2004/0076262 A1* 4/2004 Shao et al. .................... 378/196

FOREIGN PATENT DOCUMENTS

CN    1688899 A    10/2005
JP    2007-107995    4/2007

OTHER PUBLICATIONS

Combined Chinese Office Action and Search Report issued Nov. 13, 2012 in Patent Application No. 201110155031.0 with English Translation of Category of Cited Documents.

* cited by examiner

*Primary Examiner* — David Porta
*Assistant Examiner* — Shun Lee
(74) *Attorney, Agent, or Firm* — Oblon, McClelland, Maier & Neustadt, L.L.P.

(57) ABSTRACT

A radiographic apparatus according to an embodiment includes storage, a shape image capture unit, an image acquiring unit, a position acquiring unit, a conversion unit, and a positional relationship adjusting unit. The shape image capture unit captures the shape image of an examinee. The image acquiring unit acquires a shape image from the storage. The position acquiring unit acquires a position in the acquired shape image which corresponds to a region of interest. The conversion unit converts the position in the acquired shape image into a position in the captured shape image. The positional relationship adjusting unit adjusts the positional relationship between a detector and the examinee on the basis of the conversion result.

6 Claims, 12 Drawing Sheets

RADIOGRAPHIC APPARATUS, CONTROL METHOD, AND COMPUTER PROGRAM PRODUCT

CROSS-REFERENCE TO RELATED APPLICATION(S)

This application is based upon and claims the benefit of priority from Japanese Patent Application No. 2010-128914, filed on Jun. 4, 2010; the entire contents of which are incorporated herein by reference.

FIELD

Embodiments described herein relate generally to a radiographic apparatus, a control method, and a computer program product.

BACKGROUND

In recent years, nuclear medicine imaging apparatuses, such as a gamma camera, a single photon emission computed tomography (SPECT) apparatus, and a positron emission tomography (PET) apparatus, have been known. The nuclear medicine imaging apparatus includes a detector that detects radiation. The nuclear medicine imaging apparatus detects radiation emitted from an isotope or a labeled compound which is introduced into body tissues using the detector and forms the image of the dose distribution of the radiation detected by the detector, thereby reconstructing a nuclear medicine image that provides the functional information of the body tissues.

For example, a radioactive drug including a labeled compound that is frequently introduced into tumor tissues is put into the body of the examinee. Then, the nuclear medicine imaging apparatus detects radiation emitted from the labeled compound for a predetermined period of time and reconstructs a nuclear medicine image including the distribution of the tumor tissues of the examinee into which the labeled compound is introduced, thereby providing the functional information of the body tissues of the examinee.

In addition, in recent years, apparatuses have been proposed in which a nuclear medicine imaging apparatus that provides functional information is integrated with an X-ray computed tomography (X-ray CT) apparatus that provides shape information. For example, the following apparatuses have been proposed: a PET-CT apparatus in which a PET apparatus and an X-ray CT apparatus are integrated with each other; and a SPECT-CT apparatus in which a SPECT apparatus and an X-ray CT apparatus are integrated with each other.

However, in the above-mentioned technique, in some cases, the image quality of a region of interest is lower than that of other regions in the PET image.

DETAILED DESCRIPTION

According to one embodiment, a radiographic apparatus includes storage, an image acquiring unit, an image acquiring unit, a position acquiring unit, a conversion unit, a positional relationship adjusting unit. The storage is configured to store a shape image of an examinee in advance; a shape image capture unit that captures the shape image of the examinee. The image acquiring unit is configured to acquire the shape image of the examinee to be captured by the shape image capture unit which is stored in advance from the storage. The position acquiring unit is configured to acquire a position corresponding to a region of interest specified in a functional image, which is captured in association with the shape image acquired by the image acquiring unit, in the acquired shape image. The conversion unit is configured to convert the position in the shape image acquired by the position acquiring unit into a position in the captured shape image, on the basis of a correspondence between the position in the shape image captured by the shape image capture unit and the position in the acquired shape image. The positional relationship adjusting unit is configured to adjust the positional relationship between the examinee and a detector which detects radiation for generating a nuclear medicine image, on the basis of the position in the captured shape image, which is the conversion result of the conversion unit.

Hereinafter, as an example of a radiographic apparatus, a PET-CT apparatus in which a PET apparatus, which is a nuclear medicine imaging apparatus, is integrated with an X-ray CT apparatus will be described.

Figure 1:
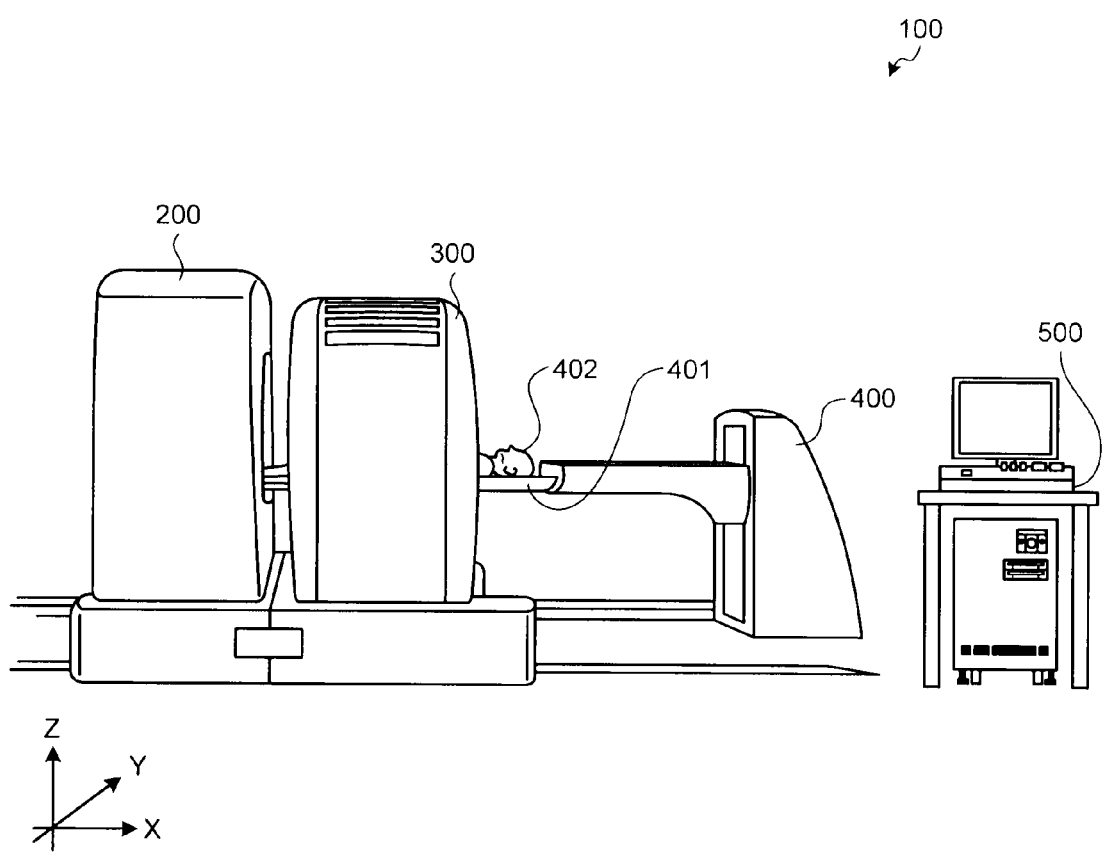
FIG. 1 is a diagram of the overall structure of a PET-CT apparatus according to a first embodiment.

FIG. 1 is a diagram illustrating the overall structure of a PET-CT apparatus according to a first embodiment. In FIG. 1, reference numeral 100 indicates a PET-CT apparatus, reference numeral 200 indicates a PET scanner, reference numeral 300 indicates an X-ray CT scanner, reference numeral 400 indicates a couch, reference numeral 401 indicates a top plate on which the examinee lies, and reference numeral 402 indicates the examinee. As shown in FIG. 1, the PET-CT apparatus 100 includes the PET scanner 200, the X-ray CT scanner 300, the couch 400, and a console 500. In FIG. 1, the X direction is the body axis direction of the examinee 402 who lies on the top plate 401 shown in FIG. 1. The Y direction is a direction on the horizontal plane that is orthogonal to the X direction. The Z direction is the vertical direction.

The couch 400 includes the top plate 401 on which the examinee 402 lies. Although not shown in FIG. 1, the couch 400 includes a couch control unit that moves the top plate 401. The couch control unit is controlled by the console 500 to move the examinee 402 on the top plate 401 into an imaging hole of the PET-CT apparatus 100. A case in which the console 500 controls the couch control unit to move the top plate 401 in the X-axis direction, the Y-axis direction, and the Z-axis direction will be described below, but the embodiment is not limited thereto. For example, the couch control unit may move the couch 400 in some of the X-axis direction, the Y-axis direction, and the Z-axis direction under the control of the console 500.

The PET scanner 200 includes a plurality of detectors 210 that detects radiation for generating a nuclear medicine image. The detectors 210 are arranged in a ring shape around the body axis of the examinee 402. For example, the detectors 210 detect a pair of gamma rays emitted from a labeled compound that is put into the body tissues of the examinee 402 on the top plate 401, from the outside of the body of the examinee 402.

Specifically, whenever the detectors 210 detect the gamma rays, the PET scanner 200 collects the detection position where the detector 210 detects the gamma rays, an energy value at the time when the gamma rays are incident on the detector 210, and the detection time when the detector 210 detects the gamma rays. The information collected by the PET scanner 200 is referred to as "count information."

Next, the relationship between the gamma ray detected by the detector 210 and a pair of gamma rays emitted from a labeled compound introduced into the body tissues of the examinee 402 will be described. The detector 210 does not always detect both a pair of gamma rays emitted from the labeled compound. For example, when a pair of gamma rays is emitted from the labeled compound, the detector 210 may detect only one of the pair of gamma rays, may detect both the pair of gamma rays, or may not detect any of the pair of gamma rays.

The labeled compound is, for example, 18F-labeled deoxyglucose that is labeled with "18F (fluorine)," which is a positron emitting nuclide. The labeled compound is given to the examinee 402 before measurement using the PET-CT apparatus 100. However, the labeled compound is not limited to the 18F labeled deoxyglucose, but any labeled compound may be used.

The X-ray CT scanner 300 includes an X-ray tube 301 that emits X-rays for generating an X-ray CT image and an X-ray detector 302 that detects the X-rays emitted by the X-ray tube 301. In the X-ray CT scanner 300, the X-ray tube 301 emits X-rays to the examinee 402 and the X-ray detector 302 detects the X-rays passing through the examinee 402. Specifically, while the X-ray CT scanner 300 is rotated about the body axis of the examinee 402, the X-ray tube 301 emits X-rays and the X-ray detector 302 detects the X-rays. That is, the X-ray CT scanner 300 emits X-rays to the examinee 402 in multiple directions while being rotated about the body axis of the examinee 402. The emitted X-rays pass through the examinee 402 and are absorbed by the examinee 402. As a result, the intensity of the X-rays is attenuated. The X-ray CT scanner 300 detects the attenuated X-rays. Data obtained by performing an amplification process or an A/D conversion process on the X-rays detected by the X-ray detector 302 is referred to as "projection data." The X-ray CT scanner 300 collects the projection data of the X-rays detected by the X-ray detector 302 and the detection position where the X-rays used to generate the projection data are detected.

Figure 2:
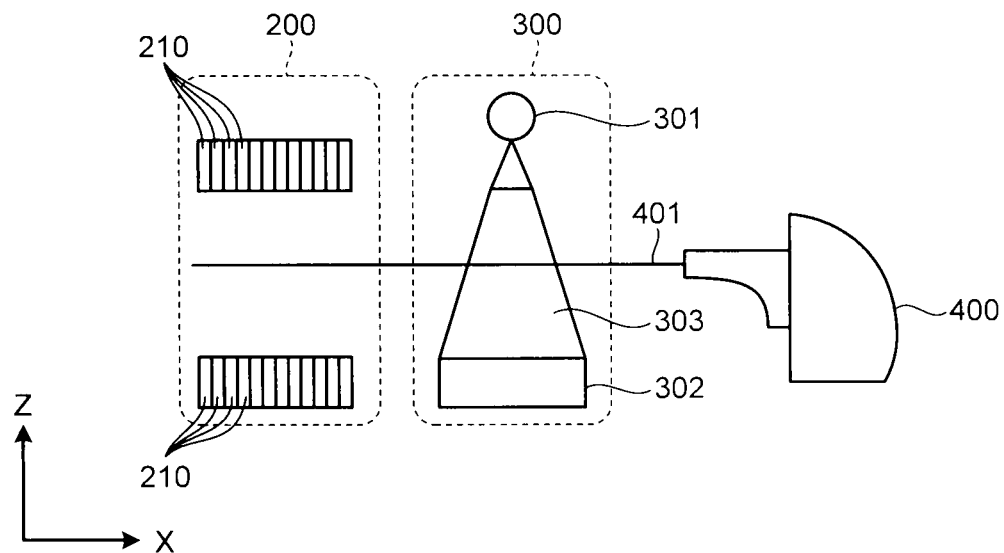
FIG. 2 is a diagram of an example of the relationship between a PET scanner and an X-ray CT scanner according to the first embodiment.

FIG. 2 is a diagram illustrating an example of the relationship between the PET scanner and the X-ray CT scanner according to the first embodiment. FIG. 2 is a cross-sectional view illustrating the PET scanner 200 and the X-ray CT scanner 300, as viewed from the Y-axis direction. In FIG. 2, reference numeral 200 indicates the PET scanner, reference numeral 210 indicates the detector, reference numeral 300 indicates an X-ray CT scanner, reference numeral 301 indicates the X-ray tube, reference numeral 302 indicates the X-ray detector, and reference numeral 303 indicates an X-ray emitted by the X-ray tube 301. For convenience of explanation, FIG. 2 shows the couch 400 and the top plate 401 in addition to the PET scanner 200 and the X-ray CT scanner 300.

As shown in FIG. 2, in the PET scanner 200, the plurality of detectors 210 is arranged in the X-axis direction. The plurality of detectors 210 is arranged so as to surround the body axis of the examinee 402 in a ring shape. As shown in FIG. 2, the X-ray CT scanner 300 includes the X-ray tube 301 and the X-ray detector 302. The X-ray tube 301 and the X-ray detector 302 are arranged so as to face each other with the top plate 401, on which the examinee 402 lies during measurement, interposed therebetween.

Figure 3:
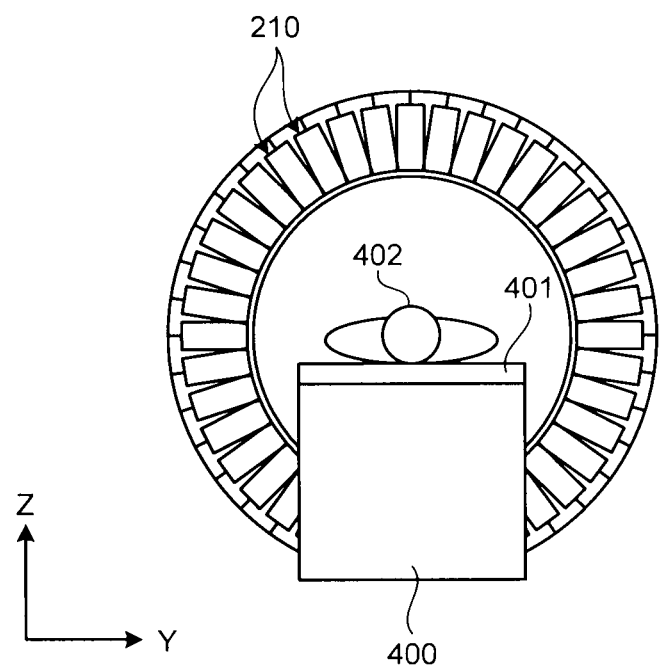
FIG. 3 is a diagram of the structure of the PET scanner according to the first embodiment.

FIG. 3 is a diagram illustrating the structure of the PET scanner according to the first embodiment. In FIG. 3, reference numeral 400 indicates the couch, reference numeral 401 indicates the top plate, reference numeral 402 indicates the examinee, and reference numeral 210 indicates the detector. FIG. 3 is a cross-sectional view illustrating the PET scanner 200, as viewed from the X-axis direction. For convenience of explanation, FIG. 3 shows the examinee 402, the couch 400, and the top plate 401 in addition to the PET scanner 200.

As shown in FIG. 3, in the PET scanner 200, the plurality of detectors 210 is arranged so as to surround the examinee 402 in a ring shape. The detector 210 is, for example, a photon counting type.

Figure 4:
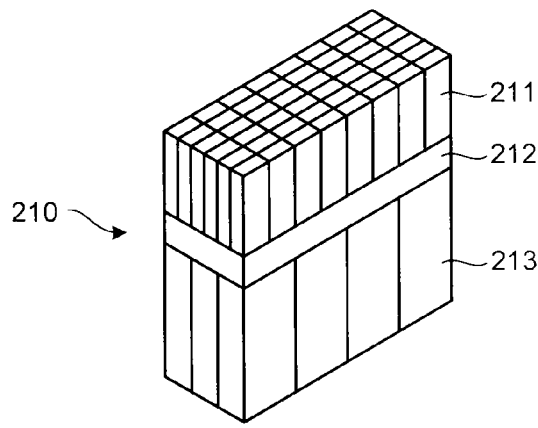
FIG. 4 is a diagram of an example of the structure of a detector according to the first embodiment.

FIG. 4 is a diagram illustrating an example of the structure of the detector according to the first embodiment. In FIG. 4, reference numeral 211 indicates a scintillator, reference numeral 212 indicates a light guide, and reference numeral 213 indicates a photomultiplier tube (PMT).

As shown in FIG. 4, the detector 210 includes the scintillator 211, the light guide 212, and the photomultiplier tube 213. The scintillator 211 converts the gamma ray that is emitted from the examinee 402 and is then incident on the detector 210 into visible light and outputs the visible light. The scintillator 211 is made of, for example, NaI or BGO that converts gamma rays into visible light. As shown in FIG. 4, the scintillators 211 are two-dimensionally arranged. The visible light output by the scintillator 211 is referred to as "scintillation light." The light guide 212 transmits the visible light output from the scintillator 211 to the photomultiplier tube 213. The light guide 212 is made of, for example, a plastic material having high light transmittance. The photomultiplier tube 213 receives the visible light output by the scintillator 211 through the light guide 212 and converts the received visible light into an electric signal. A plurality of photomultiplier tubes 213 is arranged.

Next, the photomultiplier tube 213 will be described. The photomultiplier tube 213 includes a photocathode that receives the scintillation light and generates photoelectrons, a multi-stage dynode that generates an electric field for accelerating the photoelectrons generated by the photocathode, and an anode which is an outlet through which electrons flow out. The electron emitted from the photocathode by the photoelectric effect is accelerated to the dynode and collides with the surface of the dynode. As a result, a plurality of electrons is ejected from the surface of the dynode. The phenomenon in which a plurality of electrons is ejected from the surface of the dynode is repeated over the multi-stage dynode and the number of electrons increases by geometrical progression.

For example, when receiving one scintillation light component, the anode outputs about 1,000,000 electrons. The number of electrons obtained from the anode when one scintillation light component is received is referred to as "the gain of the photomultiplier tube." In this case, the gain of the photomultiplier tube 213 is 1,000,000. In addition, a voltage of 1000 V (volt) or more is generally applied between the dynode and the anode in order to increase the number of electrons in geometrical progression.

As such, in the detector 210, the scintillator 211 converts the gamma ray into scintillation light and the photomultiplier tube 213 converts the visible light into an electric signal. In this way, the detector 210 detects the gamma ray emitted from the examinee 402.

Figure 5:
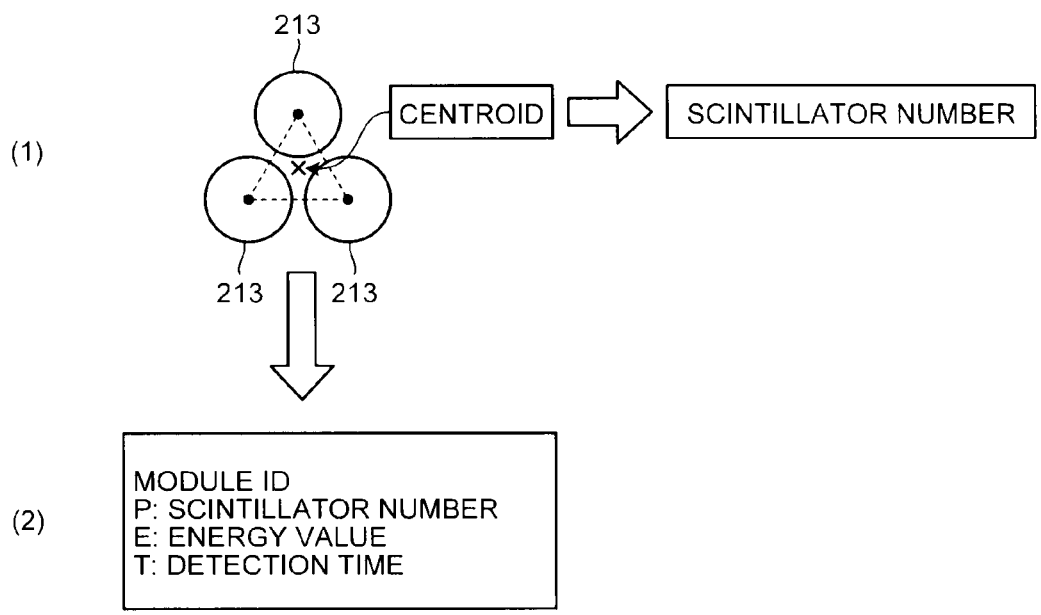
FIG. 5 is a diagram of information detected by an anger-type detector according to the first embodiment.

As described above, whenever the detector 210 detects the gamma ray, the PET scanner 200 collects the detection position, the energy value, and the detection time. Next, an example of a process of calculating the detection position and the energy value when a plurality of adjacent detectors 210 detect gamma rays at the same time will be described in brief with reference to FIG. 5. FIG. 5 is a diagram illustrating information detected by an anger-type detector according to the first embodiment.

For example, the PET scanner 200 performs an anger-type position calculating process to settle the detection position. For example, when the photomultiplier tube 213 is a position-detection-type photomultiplier tube, the PET scanner 200 collects the detection position using the position-detection-type photomultiplier tube 213. As shown in (1) of FIG. 5, a case in which three photomultiplier tubes 213 convert scintillation light into electric signals and output the electric signals at the same time will be described. In this case, the PET scanner 200 acquires the position of the photomultiplier tubes 213 that output the electric signals at the same time and acquires each of the energy values of the electric signals that are output from the photomultiplier tubes 213 at the same time. Then, the PET scanner 200 calculates the center position from the acquired energy values and specifies the scintillator 211 corresponding to the calculated center position. In addition, the PET scanner 200 integrates the energy values of the electric signals output from each of the photomultiplier tubes 213 that convert the scintillation light into electric signals and output the electric signals at the same time and uses the integrated energy value as the energy value of the gamma ray incident on the detector 210.

As shown in (2) of FIG. 5, whenever the detector 210 detects the gamma ray, the PET scanner 200 collects a "scintillator number" that uniquely identifies the scintillator 211, the "energy value," and the "detection time." In the example shown in (2) of FIG. 5, in addition to the "scintillator number," the "energy value," and the "detection time," a "module ID" which is information uniquely identifying the detector 210 is output.

The detection time may be absolute time, such as time, or the time elapsed from the start of the capture of a PET image. The detector 210 collects the detection time with an accuracy of, for example, $10^{-10}$ to $10^{-12}$ sec (psec). Then, the console 500 receives the count information from the PET scanner 200, generates coincidence information, and reconstructs the PET image using the generated coincidence information.

Next, the coincidence information generated from the count information will be described in brief and then the effective field of view and the detection sensitivity of the PET scanner 200 according to the first embodiment will be described. When a pair of gamma rays is emitted from the positron emitting nuclide and the detector 210 detects both the pair of gamma rays, the detector 210 collects two count information items each time the gamma rays are emitted from the positron emitting nuclide. The coincidence information is a combination of two count information items collected whenever the gamma rays are emitted from the positron emitting nuclide. That is, a pair of gamma rays is emitted from any point on a straight line linking the detection positions which are included in two count information items in the coincidence information. The PET image is reconstructed using the fact that the positron emitting nuclide emitting a pair of gamma rays is disposed on the straight line linking two detection positions which are included in the coincidence information. As a result, as the number of coincidence information items increases, the quality of the PET image is improved. As the number of coincidence information items is reduced, the quality of the PET image deteriorates. In addition, the coincidence information includes two count information items whenever the gamma rays are emitted from the positron emitting nuclide. As a result, when the detector 210 detects both a pair of gamma rays, the coincidence information is generated. However, when the detector 210 detects only one of the pair of gamma rays, the coincidence information is not generated.

Figure 6:
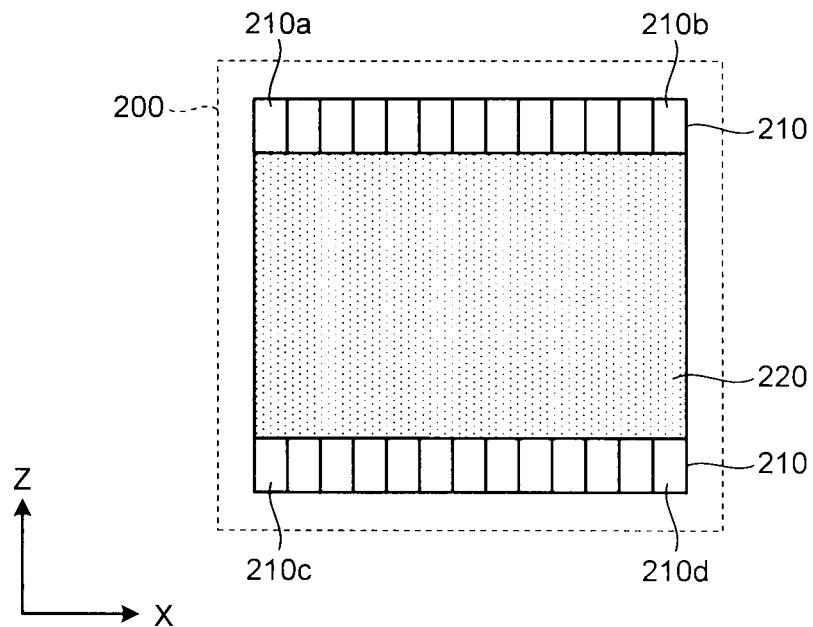
FIG. 6 is a diagram of the effective field of view of the PET scanner according to the first embodiment.

FIG. 6 is a diagram illustrating the effective field of view of the PET scanner according to the first embodiment. FIG. 6 is a cross-sectional view illustrating the PET scanner 200 taken along the XZ plane, as viewed from the Y-axis direction. In FIG. 6, reference numeral 210 indicates a detector. Reference numeral 210a indicates the leftmost detector 210 in a group of the detectors 210 disposed on the upper side of FIG. 6, reference numeral 210b indicates the rightmost detector 210 in the group of the detectors 210 disposed on the upper side of FIG. 6, reference numeral 210c indicates the leftmost detector 210 in a group of the detectors 210 disposed on the lower side of FIG. 6, and reference numeral 210d indicates the rightmost detector 210 in the group of the detectors 210 disposed on the lower side of FIG. 6. Reference numeral 220 indicates the effective field of view of the PET scanner 200.

When the detector 210 does not detect both a pair of gamma rays, the coincidence information is not generated. In light of this, the PET scanner 200 shown in FIG. 6 can detect both the pair of gamma rays in the range surrounded by a straight line linking the detector 210a and the detector 210c and a straight line linking the detector 210b and the detector 210d, as in the effective field of view 220 shown in FIG. 6.

Figure 7:
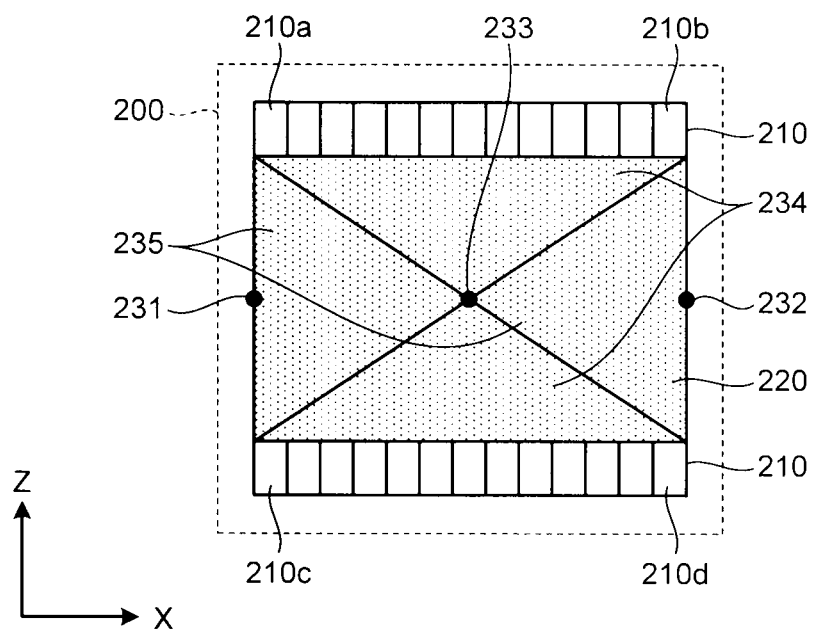
FIG. 7 is a diagram of the detection sensitivity of the PET scanner according to the first embodiment.

FIG. 7 is a diagram illustrating the detection sensitivity of the PET scanner according to the first embodiment. FIG. 7 is a cross-sectional view illustrating the PET scanner 200 taken along the XZ plane, as viewed from the Y-axis direction. In FIG. 7, reference numerals 231 to 233 indicate positions in the effective field of view 220. The position 231 is the end of the effective field of view of the PET scanner 200 and is on the straight line linking the detector 210a and the detector 210c. The position 232 is the end of the effective field of view of the PET scanner 200 and is on the straight line linking the detector 210b and the detector 210d. The position 233 is the center of the effective field of view of the PET scanner 200 where the straight line linking the detector 210a and the detector 210d intersects the straight line linking the detector 210b and the detector 210c. Reference numeral 234 indicates a region surrounded by the groups of the detectors 210 disposed on the upper and lower sides of the FIG. 6, the straight line linking the detector 210a and the detector 210d, and the straight line linking the detector 210b and the detector 210c. Reference numeral 235 indicates a region surrounded by the straight line linking the detector 210a and the detector 210c or the straight line linking the detector 210b and the detector 210d, the straight line linking the detector 210a and the detector 210d, and the straight line linking the detector 210b and the detector 210c.

In the example shown in FIG. 7, when a pair of gamma rays is emitted at the position 231, the pair of gamma rays is emitted to the detector 210a and the detector 210c. When the detector 210a and the detector 210c detect the gamma rays, coincidence information is generated first. That is, when a pair of gamma rays is emitted at the position 231, but the detector 210a or the detector 210c is not disposed in the traveling direction of the pair of gamma rays, the detector 210 does not detect both the pair of gamma rays emitted at the position 231. As a result, the coincidence information is not generated. The same result as described above is obtained at the position 232.

When a pair of gamma rays is emitted at the position 233 and travels toward the region 234, the detectors 210 of the PET scanner 200 can detect both the pair of gamma rays and the coincidence information is generated. That is, in the example shown in FIG. 7, the PET scanner 200 can detect the gamma rays emitted from the position 233 using all of the upper detectors 210 and the lower detectors 210, unlike the position 231 or the position 232.

As such, in the PET scanner 200, the number of pairs of gamma rays detected at the position deviating from the center of the effective field of view is smaller than that detected at the center of the effective field of view. When the number of detected gamma rays is reduced, the quality of the PET image deteriorates. That is, when the number of detected gamma rays is reduced, the detection sensitivity is reduced. In other words, in the PET scanner 200, as the distance from the center of the effective field of view increases, the detection sensitivity is reduced.

Figure 8:
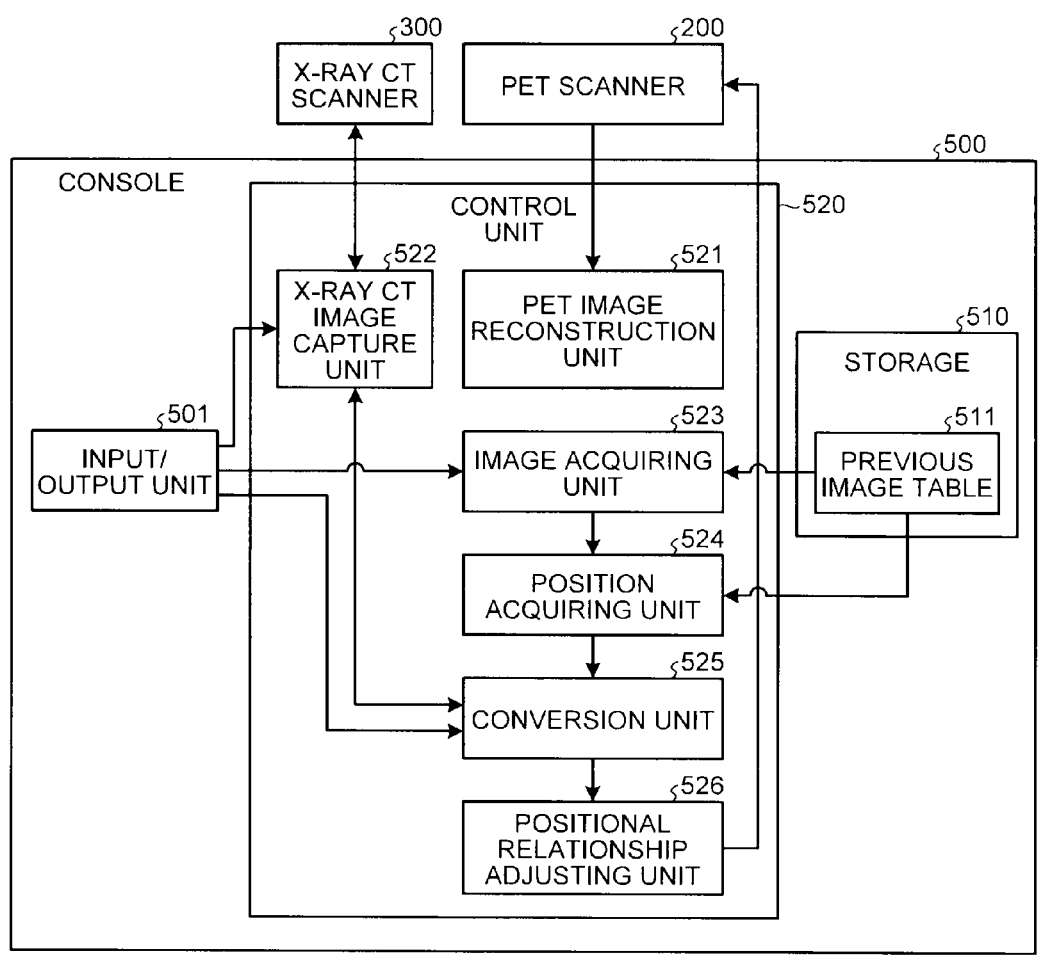
FIG. 8 is a block diagram of an example of the structure of a console according to the first embodiment.

FIG. 8 is a block diagram illustrating an example of the structure of the console according to the first embodiment. The console 500 places a region of interest at the center of the effective field of view of the PET scanner 200, controls the PET scanner 200 to collect the count information, generates coincidence information from the count information collected by the PET scanner 200, and reconstructs a PET image, which will be described in detail below.

For convenience of explanation, FIG. 8 shows the PET scanner 200 and the X-ray CT scanner 300 in addition to the console 500. In the example shown in FIG. 8, the console 500 includes an input/output unit 501, storage 510, and a control unit 520.

The input/output unit 501 is connected to the control unit 520. The input/output unit 501 receives various kinds of instructions from the user of the PET-CT apparatus 100 and transmits the received instructions to the control unit 520. The input/output unit 501 receives information from the control unit 520 and outputs the received information to the user. For example, the input/output unit 501 is a keyboard, a mouse, a microphone, a monitor, or a speaker. A description of the details of the information or instruction received by the input/output unit 501 or the details of the information output by the input/output unit 501 will be described here, but the details of the information or instruction will be described below together with each unit related thereto.

The storage 510 is connected to the control unit 520. The storage 510 stores data used in various kinds of processes of the control unit 520. The storage 510 is, for example, a semiconductor memory device, such as a random access memory (RAM) or a flash memory, or a storage device, such as a hard disk or an optical disk. In the example shown in FIG. 8, the storage 510 includes a previous image table 511.

The previous image table 511 stores the shape image and the functional image of the examinee in advance so as to be associated with each other. Specifically, the previous image table 511 stores the previously captured X-ray CT image and PET image of the examinee so as to be associated with identification information for identifying the examinee. The X-ray CT image and PET image that are stored so as to be associated with each other in the previous image table 511 correspond to, for example, the X-ray CT image and PET image of the same examinee previously captured by the PET-CT apparatus 100. A position in the shape image and a position in the functional image are associated with each other. That is, when one position in the functional image is designated, a position in the shape image corresponding to the designated position is specified.

Figure 9:
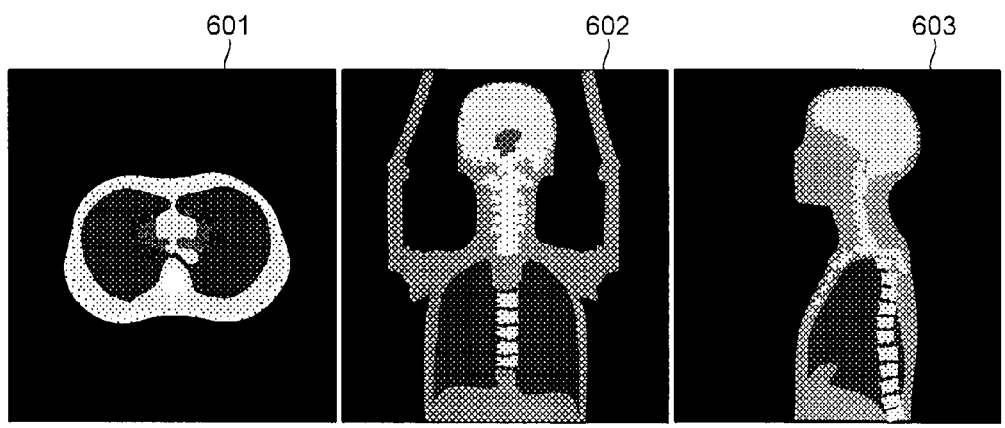
FIG. 9 is a diagram of an example of a shape image stored in a previous image table according to the first embodiment.

FIG. 9 is a diagram illustrating an example of the shape image stored in the previous image table according to the first embodiment. In FIG. 9, reference numeral 601 indicates an X-ray CT image in the axial plane of the examinee, reference numeral 602 indicates an X-ray CT image in the coronal plane of the examinee, and reference numeral 603 indicates an X-ray CT image in the sagittal plane of the examinee. That is, reference numeral 601 indicates the tomographic image of the examinee in the YX plane of FIG. 1, reference numeral 602 indicates the tomographic image of the examinee in the XY plane, and reference numeral 603 indicates the tomographic image of the examinee in the XZ plane. Hereinafter, the X-ray CT image of the examinee in the axial surface is referred to as an "axial image," the X-ray CT image of the examinee in the coronal plane is referred to as a "coronal image," and the X-ray CT image of the examinee in the sagittal plane is referred to as a "sagittal image."

In the example shown in FIG. 9, the previous image table 511 stores the axial image, the coronal image, and the sagittal image as the shape images so as to be associated with the identification information for identifying the examinee. However, the embodiment is not limited to the structure in which the previous image table 511 stores the axial image, the coronal image, and the sagittal image. For example, the previous image table 511 may not store some of the axial image, the coronal image, and the sagittal image. For example, the previous image table 511 may store projection data obtained by the X-ray CT scanner 300 and the control unit 520 may reconstruct the axial image, the coronal image, the sagittal image from the projection data stored in the previous image table 511.

The previous image table 511 may store the image that has been previously captured by the PET-CT apparatus 100 or the image captured by other apparatuses.

The control unit 520 is connected to the input/output unit 501 and the storage 510. The control unit 520 includes an internal memory that stores programs for defining, for example, various kinds of procedures and controls various kinds of processes. The control unit 520 corresponds to an electronic circuit, such as an application specific integrated circuit (ASIC), a field programmable gate array (FPGA), a central processing unit (CPU), or a micro processing unit (MPU). In the example shown in FIG. 8, the control unit 520 includes a PET image reconstruction unit 521, an X-ray CT image capture unit 522, an image acquiring unit 523, a position acquiring unit 524, a conversion unit 525, and a positional relationship adjusting unit 526.

The PET image reconstruction unit 521 receives the count information collected by the PET scanner 200 and reconstructs the PET image on the basis of the received count information. Specifically, the PET image reconstruction unit 521 searches for a composition of count information items indicating a pair of gamma rays on the basis of the energy value and the detection time included in the received count information, and generates coincidence information. Then, the PET image reconstruction unit 521 reconstructs the PET image using the generated coincidence information. Searching for a combination of count information items indicating a pair of gamma rays is referred to as "coincidence finding." In addition, a list of the coincidence information items generated by the PET image reconstruction unit 521 is referred to as a "coincidence list." The PET image reconstruction unit 521 performs a PET dynamic imaging operation of capturing a plurality of PET images of a part of the body in time series.

In the control unit 520, the X-ray CT image capture unit 522, the image acquiring unit 523, the position acquiring unit 524, the conversion unit 525, and the positional relationship adjusting unit 526 place the region of interest at the center of the effective field of view of the PET scanner 200 in cooperation with each other. Then, the control unit 520 controls the PET scanner 200 to collect the count information, which will be described below. That is, the PET scanner 200 compares the detection efficiency of a pair of radiations emitted from the region of interest of the examinee with the detection efficiency of a pair of radiations emitted from other regions of the examinee and collects the count information in the stage in which the detection efficiency is improved. As a result, the PET image reconstruction unit 521 reconstructs the PET image on the basis of the count information received from the PET scanner 200, thereby reconstructing the PET image in which the image quality of the region of interest is higher than that of other regions. The PET image reconstruction unit 521 may reconstruct the PET image using any method, such as successive approximation, and a detailed description thereof will be not be made.

Returning to FIG. 8, in the control unit 520, the X-ray CT image capture unit 522, the image acquiring unit 523, the position acquiring unit 524, the conversion unit 525, and the positional relationship adjusting unit 526 place the region of interest at the center of the effective field of view of the PET scanner 200 in cooperation with each other. Then, the control unit 520 controls the PET scanner 200 to collect the count information.

When receiving an imaging instruction to capture the PET image of the examinee from the user through the input/output unit 501, the X-ray CT image capture unit 522 operates the X-ray CT scanner 300 to capture an X-ray CT image. Specifically, the X-ray CT image capture unit 522 receives projection data from the X-ray CT scanner 300 and reconstructs the received projection data, thereby capturing the X-ray CT image. The shape image captured by the X-ray CT image capture unit 522 is referred to as a "captured shape image."

For example, the X-ray CT image capture unit 522 operates the X-ray CT scanner 300 and receives the X-ray projection data and the X-ray detection position collected by the X-ray CT scanner 300. For example, the X-ray CT image capture unit 522 stores the X-ray projection data and the X-ray detection position in a table (not shown in FIG. 8) of the storage 510. Then, the X-ray CT image capture unit 522 reconstructs the X-ray CT image using the received X-ray projection data and X-ray detection position, thereby reconstructing the axial image, the coronal image, and the sagittal image of the examinee.

However, the shape image capture process of the X-ray CT image capture unit 522 is not limited to the above. For example, the X-ray CT image capture unit 522 may control the X-ray tube 301 of the X-ray CT scanner 300 to emit X-rays while moving along the body axis of the examinee 402, without being rotated about the body axis of the examinee 402, thereby capturing a scanoscope image. Specifically, the X-ray CT image capture unit 522 may capture a scanoscope image in the coronal plane and capture a scanoscope image in the sagittal plane.

Figure 10:
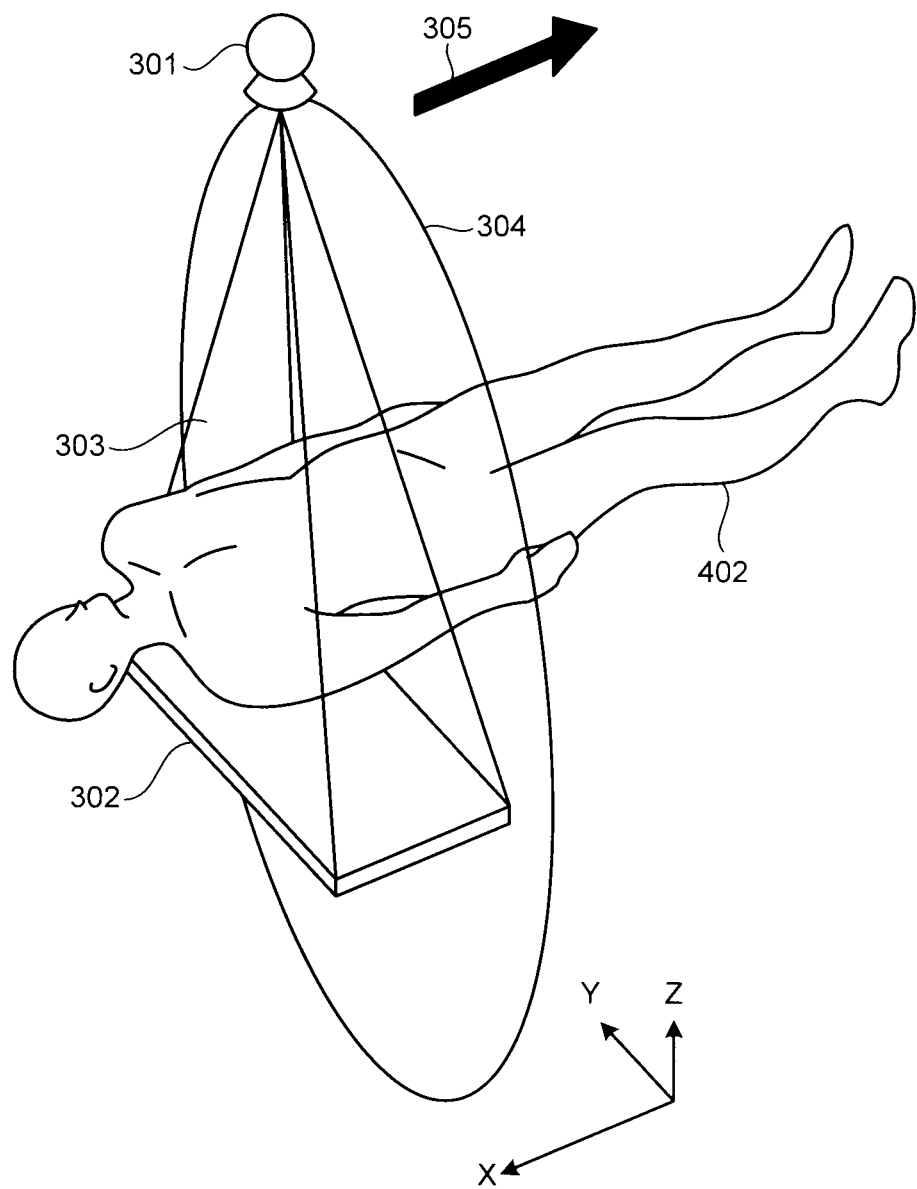
FIG. 10 is a diagram of the capture of a scanoscope image.

FIG. 10 is a diagram illustrating the capture of the scanoscope image. In FIG. 10, reference numeral 304 indicates a trajectory when the X-ray tube 301 is rotated about the body axis of the examinee 402. When the X-ray tube 301 of the X-ray CT scanner 300 emits X-rays while being rotated about the body axis of the examinee 402, the X-ray tube 301 moves the trajectory 304. In FIG. 10, reference numeral 305 is an arrow indicating the moving direction of the X-ray tube 301 when the scanoscope image is captured.

As represented by the arrow 305 in FIG. 10, when the scanoscope image is captured, the X-ray tube 301 emits the X-rays while being moved in the X-axis direction, without being rotated. FIG. 10 shows an example in which the X-ray tube 301 emits the X-rays to the examinee 402 in the Z-axis direction. Therefore, in the example shown in FIG. 10, the X-ray CT image capture unit 522 captures the scanoscope image of the examinee 402 in the coronal plane in the XY plane. When the scanoscope image of the examinee 402 in the sagittal plane in the ZX plane is captured, the X-ray tube 301 emits the X-rays in the Y-axis direction from the side of the examinee 402 while being moved on the X-axis.

Returning to FIG. 8, when receiving an imaging instruction to capture the PET image of the examinee from the user through the input/output unit 501, the image acquiring unit 523 acquires the stored shape image of the examinee to be captured by the PET-CT apparatus 100 from the previous image table 511. For example, when receiving identification information for identifying the examinee from the user through the input/output unit 501, the image acquiring unit 523 acquires the axial image, the coronal image, and the sagittal image which are associated with the received identification information. That is, the image acquiring unit 523 acquires the previously captured axial image, coronal image, and sagittal image of the examinee. The shape image acquired by the image acquiring unit 523 is referred to as an "acquired shape image." The examinee whose image is captured by the PET-CT apparatus 100 is referred to as a "captured examinee."

The position acquiring unit 524 acquires a position corresponding to the region of interest specified in the functional image which is captured in association with the acquired shape image, which is the shape image acquired by the image acquiring unit 523, in the acquired shape image. For example, the position acquiring unit 524 acquires a functional image associated with the shape image acquired by the image acquiring unit 523 from the previous image table 511 and acquires the position of the region of interest in the acquired functional image.

Specifically, the position acquiring unit 524 acquires a PET image associated with the shape image acquired by the image acquiring unit 523 from the previous image table 511. Then, the position acquiring unit 524 specifies a region with a pixel value greater than that of other regions in the PET image and acquires a position in the acquired shape image which is associated with the specified position in the PET image.

The conversion unit 525 converts the position in the shape image which is acquired by the position acquiring unit 524 into a position in the captured shape image on the basis of the correspondence between the position in the captured shape image and the position in the acquired shape image. That is, the conversion unit 525 converts a position in the previously captured shape image into a position in the currently captured shape image.

Figure 11:
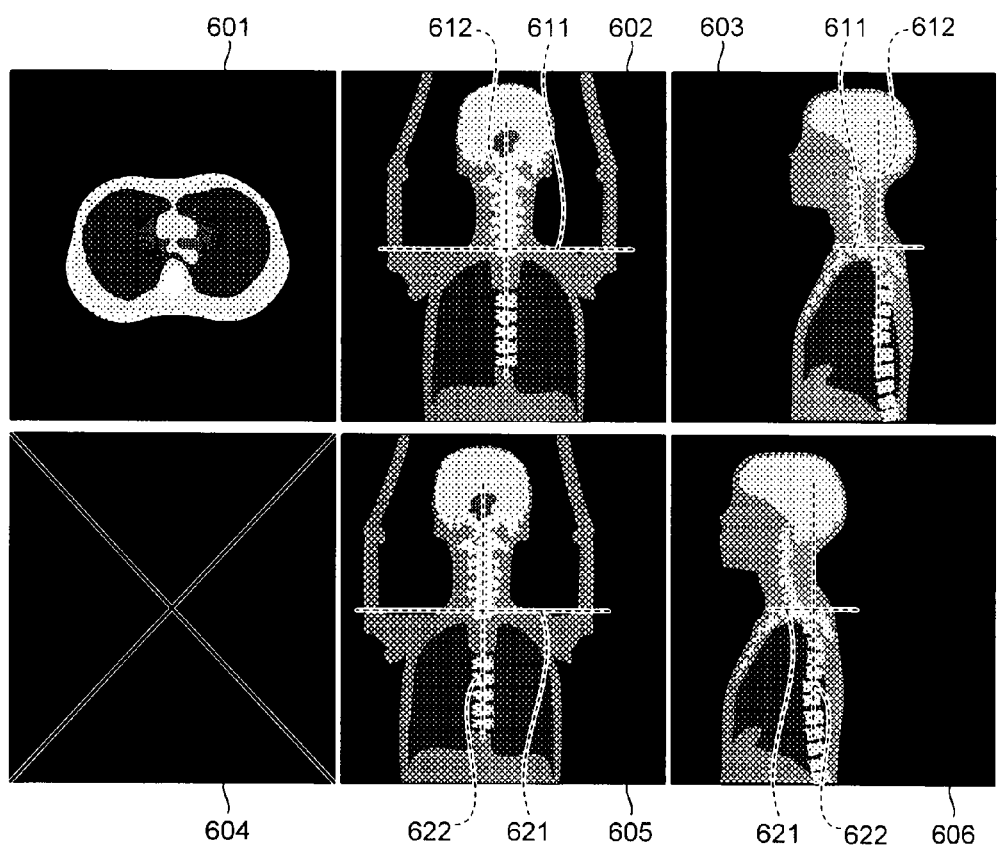
FIG. 11 is a diagram of the identification of the correspondence between a position in a captured shape image and a position in an acquired shape image.

Specifically, the conversion unit 525 identifies the correspondence between a position in the captured shape image and a position in the acquired shape image. That is, the conversion unit 525 identifies the correspondence between a position in the shape image of the examinee that has been previously captured and then stored in the previous image table 511 and a position in the newly captured shape image of the examinee. FIG. 11 is a diagram illustrating the identification of the correspondence between a position in the captured shape image and a position in the acquired shape image. In FIG. 11, reference numerals 601 to 603 indicate the acquired shape images that are stored in the previous image table 511 in advance. That is, reference numerals 601 to 603 indicate, for example, the previously captured shape images of the examinee. Reference numerals 604 to 606 indicate the shape images captured by the X-ray CT image capture unit 522. That is, reference numerals 604 to 606 indicate the newly captured shape images of the examinee. Reference numeral 601 indicates an axial image, reference numerals 602 and 605 indicate coronal images, and reference numerals 603 and 606 indicate sagittal images. FIG. 11 shows an example in which the X-ray CT image capture unit 522 captures the scanoscope image in the coronal plane and captures the scanoscope image in the sagittal plane. That is, FIG. 11 shows an example in which the X-ray CT image capture unit 522 does not capture a new axial image.

For example, the conversion unit 525 identifies a characteristic portion of the examinee in the captured shape image. In the example shown in FIG. 11, the conversion unit 525 identifies a position 611 of the shoulder blade and a position 612 of the backbone of the examinee with the coronal image 602 and identifies the position 611 of the shoulder blade and the position 612 of the backbone of the examinee with the sagittal image 603. Then, for example, the conversion unit 525 identifies a characteristic portion of the examinee in the acquired shape image. In the example shown in FIG. 11, the conversion unit 525 identifies a position 621 of the shoulder blade and a position 622 of the backbone of the examinee with the coronal image 605 and identifies the position 621 of the shoulder blade and the position 622 of the backbone of the examinee with the sagittal image 606.

For example, the conversion unit 525 associates the position of the characteristic portion of the examinee identified in the captured shape image with the position of the characteristic portion identified in the acquired shape image to identify the correspondence between the position in the captured shape image and the position in the acquired shape image. In the example shown in FIG. 11, the conversion unit 525 identifies that the position 621 in the acquired shape image corresponds to the position 611 in the captured shape image and the position 622 in the acquired shape image corresponds to the position 612 in the captured shape image. In addition, the conversion unit 525 identifies the correspondence between positions other than the position 611 or 612 in the acquired shape image and positions in the captured shape image on the basis of the distance from the position 611 or 612.

In this case, when the scale of the acquired image of the examinee is different from that of the captured shape image of the examinee, the conversion unit 525 identifies the correspondence between the images considering the difference between the scales.

Specifically, the conversion unit 525 converts a position in the shape image acquired by the position acquiring unit 524 into a position in the captured shape image on the basis of the identified correspondence. The position in the shape image acquired by the position acquiring unit 524 indicates the position of the region of interest. That is, the conversion unit 525 acquires the position of the region of interest in a newly captured shape image.

Figure 12:
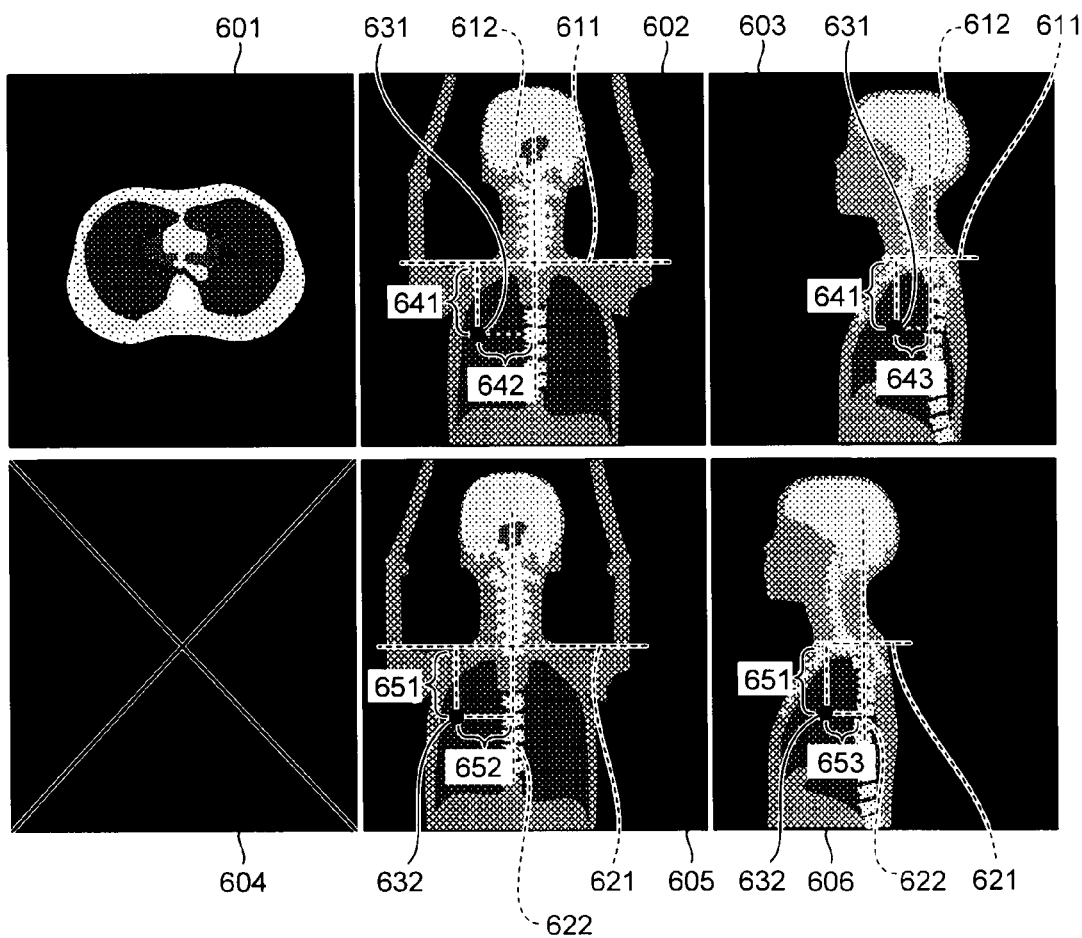
FIG. 12 is a diagram of the conversion of a position in the first embodiment.

FIG. 12 is a diagram illustrating the conversion of the position according to the first embodiment. In FIG. 12, reference numeral 631 indicates a position in the acquired shape image which corresponds to the region of interest. That is, reference numeral 631 indicates, for example, the position of the region of interest in the previously captured shape image of the examinee. Reference numeral 632 indicates a position in the captured shape image which corresponds to the position 631. Reference numeral 641 indicates a distance between the position 631 and the position 611 on the X-axis, reference numeral 642 indicates a distance between the position 631 and the position 612 on the Y-axis, and reference numeral 643 indicates a distance between the position 631 and the position 612 on the Z-axis. Reference numeral 651 indicates a distance between the position 632 and the position 621 on the X-axis, reference numeral 652 indicates a distance between the position 632 and the position 622 on the Y-axis, and reference numeral 653 indicates a distance between the position 632 and the position 622 on the Z-axis.

A case in which the scale of the acquired shape image is equal to that of the captured shape image will be described. For example, the conversion unit 525 identifies the distance 641, the distance 642, and the distance 643. Then, for example, the conversion unit 525 identifies the position where the distance from the position 611 on the X-axis is the distance 641, the distance from the position 612 on the Y-axis is the distance 642, and the distance from the position 612 on the Z-axis is the distance 643 in the captured shape image. That is, the conversion unit 525 identifies the position where the distance 641 is equal to the distance 651, the distance 642 is equal to the distance 652, and the distance 643 is equal to the distance 653 in the captured shape image. Then, the conversion unit 525 uses the identified position as a converted position.

The positional relationship adjusting unit 526 adjusts the positional relationship between the detector 210 and the examinee on the basis of the position in the captured shape image, which is the conversion result of the conversion unit 525. Specifically, the positional relationship adjusting unit 526 adjusts the positional relationship such that the detection efficiency of a pair of radiations emitted from the positron emitting nuclide at the position, which is the conversion result of the conversion unit 525, is more than that of a pair of radiations emitted from the positron emitting nuclide at other positions. That is, the positional relationship adjusting unit 526 adjusts the positional relationship such that the position, which is the conversion result of the conversion unit 525, is the center of the effective field of view of the PET scanner 200.

Specifically, the positional relationship adjusting unit 526 moves the position of the top plate 401 of the couch 400 in the X-axis direction, the Y-axis direction, and the Z-axis direction such that the position, which is the conversion result of the conversion unit 525, is the center of the effective field of view. For example, in the example shown in FIG. 12, the positional relationship adjusting unit 526 moves the top plate 401 such that the position 632 is the center of the effective field of view. As a result, in the PET-CT apparatus 100, the region of interest is disposed at the center of the effective field of view and image quality in the region of interest is more than that in other regions.

Figure 13:
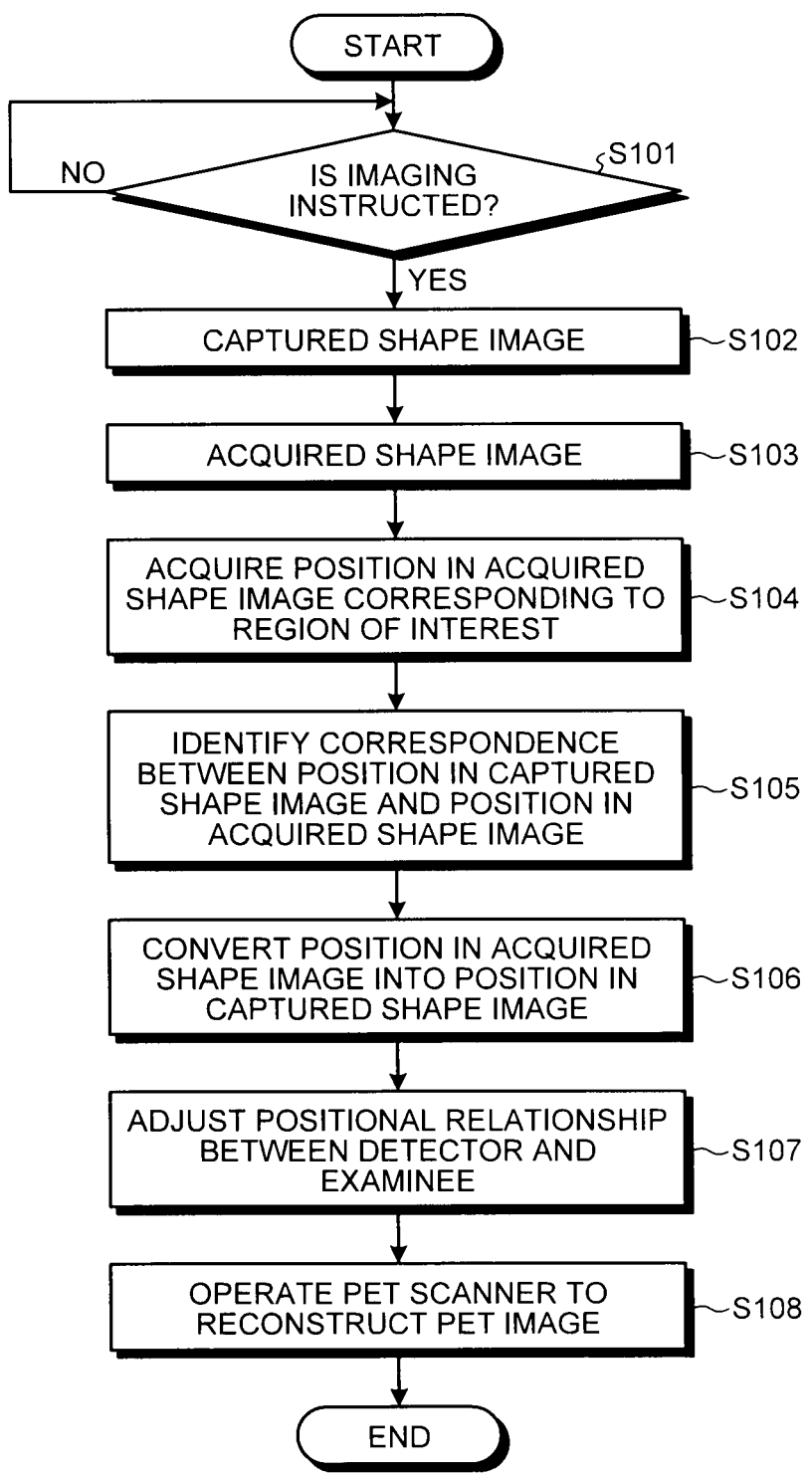
FIG. 13 is a flowchart of an example of the flow of the process of the PET-CT apparatus according to the first embodiment.

Next, an example of the flow of the process of the PET-CT apparatus 100 according to the first embodiment will be described with reference to FIG. 13. FIG. 13 is a flowchart illustrating an example of the flow of the process of the PET-CT apparatus according to the first embodiment.

As shown in FIG. 13, in the PET-CT apparatus 100, when an imaging instruction is received (Step S101: Yes), the X-ray CT image capture unit 522 operates the X-ray CT scanner 300 to capture an X-ray CT image (Step S102). That is, the X-ray CT image capture unit 522 captures a captured shape image. For example, the X-ray CT image capture unit 522 captures a scanoscope image in the coronal plane and captures a scanoscope image in the sagittal plane.

The image acquiring unit 523 acquires the shape image that has been stored in advance (Step S103). That is, the image acquiring unit 523 acquires the acquired shape image. For example, the image acquiring unit 523 acquires the previously captured axial image, coronal image, and sagittal image of the examinee.

Then, the position acquiring unit 524 acquires a position in the acquired shape image which corresponds to the region of interest (Step S104). For example, the position acquiring unit 524 specifies a region with a pixel value greater than that of other regions in the PET image associated with the acquired shape image and acquires a position in the acquired shape image which is associated with the specified position in the PET image.

Then, the conversion unit 525 identifies the correspondence between the position in the captured shape image and the position in the acquired shape image (Step S105). For example, the conversion unit 525 identifies the position 611 of the shoulder blade and the position 612 of the backbone of the examinee in the captured shape image and identifies the position 621 of the shoulder blade and the position 622 of the backbone of the examinee in the acquired shape image. Then, the conversion unit 525 associates the position identified in the captured shape image with the position identified in the acquired shape image to identify the correspondence between the position in the captured shape image and the position in the acquired shape image. Then, the conversion unit 525 converts a position in the shape image acquired by the position acquiring unit 524 into a position in the captured shape image on the basis of the identified correspondence (Step S106).

Then, the positional relationship adjusting unit 526 adjusts the positional relationship between the detector 210 and the examinee on the basis of the position in the captured shape image, which is the conversion result of the conversion unit 525 (Step S107). For example, the positional relationship adjusting unit 526 adjusts the positional relationship such that the position in the captured shape image, which is the conversion result of the conversion unit 525, is the center of the effective field of view of the PET scanner 200.

Then, the PET image reconstruction unit 521 operates the PET scanner 200 to reconstruct a PET image (Step S108).

The procedure is not limited to the above-mentioned sequence, but it may be appropriately changed within the range in which the content of the process is consistent. For example, Step S102 may be performed before Step S101, or Steps S102 and S101 may be performed at the same time.

As described above, according to the first embodiment, the PET-CT apparatus 100 stores the shape image of the examinee in advance. In addition, the PET-CT apparatus 100 acquires the shape image of the examinee that is stored in advance from the previous image table 511 and acquires a position corresponding to the region of interest specified in the functional image which is captured in association with the acquired shape image, in the acquired shape image. Then, the PET-CT apparatus 100 converts the position in the acquired shape image into a position in the captured shape image on the basis of the correspondence between the position in the captured shape image and the position in the acquired shape image. Then, the PET-CT apparatus 100 adjusts the positional relationship between the detector 210 and the examinee on the basis of the position in the captured shape image, which is the conversion result. As a result, it is possible to improve the detection efficiency of a pair of radiations emitted from the positron emitting nuclide in the region of interest to be more than that a pair of radiations emitted from the positron emitting nuclide in other regions and improve image quality in the region of interest to be more than that in other regions.

As described above, according to the first embodiment, the PET-CT apparatus 100 adjusts the positional relationship between the detector 210 and the examinee such that the position, which is the conversion result of the position conversion unit, is the center of the effective field of view of the PET scanner 200. As a result, it is possible to improve the detection efficiency of a pair of radiations emitted from the positron emitting nuclide in the region of interest to be more than that a pair of radiations emitted from the positron emitting nuclide in other regions and improve image quality in the region of interest to be more than that in other regions.

The first embodiment has been described above, but the embodiment is not limited thereto. Other embodiments may be achieved. Next, other embodiments will be described.

For example, in the above-described embodiment, the X-ray CT scanner 300 is used to capture the shape image of the examinee. However, the X-ray CT scanner 300 may not be used to capture the shape image. Other imaging apparatuses may be used to capture the shape image. For example, a magnetic resonance imaging (MRI) apparatus may be used to capture the shape image.

In the above-described embodiment, the previous image table 511 stores the X-ray CT image as the shape image. However, the previous image table 511 may not store the X-ray CT image. The previous image table 511 may store other shape images. For example, the previous image table 511 may store an MRI image.

For example, in the above-described embodiment, the previous image table 511 stores the shape image and the functional image, but the embodiment is not limited thereto. For example, the previous image table 511 may store the shape image and the position of the region of interest in the shape image so as to be associated with each other. The position of the region of interest in the shape image is specified in the functional image that is captured in association with the shape image.

For example, the previous image table 511 may store only the shape image. In this case, for example, the PET-CT apparatus 100 receives a position corresponding to a region of interest in the shape image stored in the previous image table 511 from the user.

For example, in the above-described embodiment, the position acquiring unit 524 specifies a region with a pixel value greater than that of other regions in the PET image, but the embodiment is not limited thereto. For example, the position acquiring unit 524 may acquire the functional image associated with the shape image which is acquired by the image acquiring unit 523 from the previous image table 511 and output the acquired functional image to the user. In this case, the position acquiring unit 524 may receive the position of a region of interest in the output functional from the user and acquire a position in the shape image which is associated with the received position.

For example, the X-ray CT image capture unit 522 may set the dose of radiation emitted from the X-ray CT scanner 300 to be less than a normal value and then acquire an X-ray CT image or a scanoscope image. As described above, this is because the shape image acquired by the X-ray CT image capture unit 522 is merely used for position alignment. As a result, it is possible to reduce the dose of radiation emitted to the examinee.

For example, in the above-described embodiment, the conversion unit 525 identifies a characteristic portion of the examinee and uses it to identify the correspondence between the positions. However, the embodiment is not limited thereto. For example, the conversion unit 525 may output the acquired shape image and the captured shape image to the user and the user may set the correspondence between the acquired shape image and the captured shape image.

For example, in the above-described embodiment, the position of the top plate is moved in the X-axis direction, the Y-axis direction, and the Z-axis direction, but the embodiment is not limited thereto. For example, when the position of the top plate is moved in the X-axis direction and the Y-axis direction, but is not moved in the Z-axis direction, it may be moved in the X-axis direction and the Y-axis direction.

For example, when there is a plurality of regions of interest and the position acquiring unit 524 acquires a plurality of positions, the positional relationship adjusting unit 526 may calculate the center of the plurality of positions and adjust the positional relationship such that the calculated center position is the center of the effective field of view of the PET scanner 200. The operator may designate one position that is determined to be important among the plurality of positions. As a result, it is possible to accurately capture the function image of each of the plurality of regions of interest.

For example, in the above-described embodiment, the console 500 receives the count information from the PET scanner 200, but the embodiment is not limited thereto. For example, the console 500 may receive the detection result of the detector 210 from the PET scanner 200. In this case, the console 500 receives waveform data output from the photomultiplier tube 213 and generates count information from the received waveform data.

For example, in the above-described embodiment, the console 500 receives the count information from the PET scanner 200 and generates the coincidence information. However, the embodiment is not limited thereto. For example, the PET scanner 200 may generate the coincidence information from the count information and transmit the generated coincidence information to the console 500.

For example, in the above-described embodiment, the PET-CT apparatus is used. However, the embodiment is not limited thereto, but any imaging apparatus may be used. For example, a SPECT-CT apparatus, a PET-magnetic resonance imaging (MRI) apparatus, or a SPECT-MRI apparatus may be used.

For example, the previous image table 511 may store any image indicating the shape of the examinee as the shape image of the examinee. For example, the previous image table 511 may store the scanoscope image of the examinee.

Figure 14:
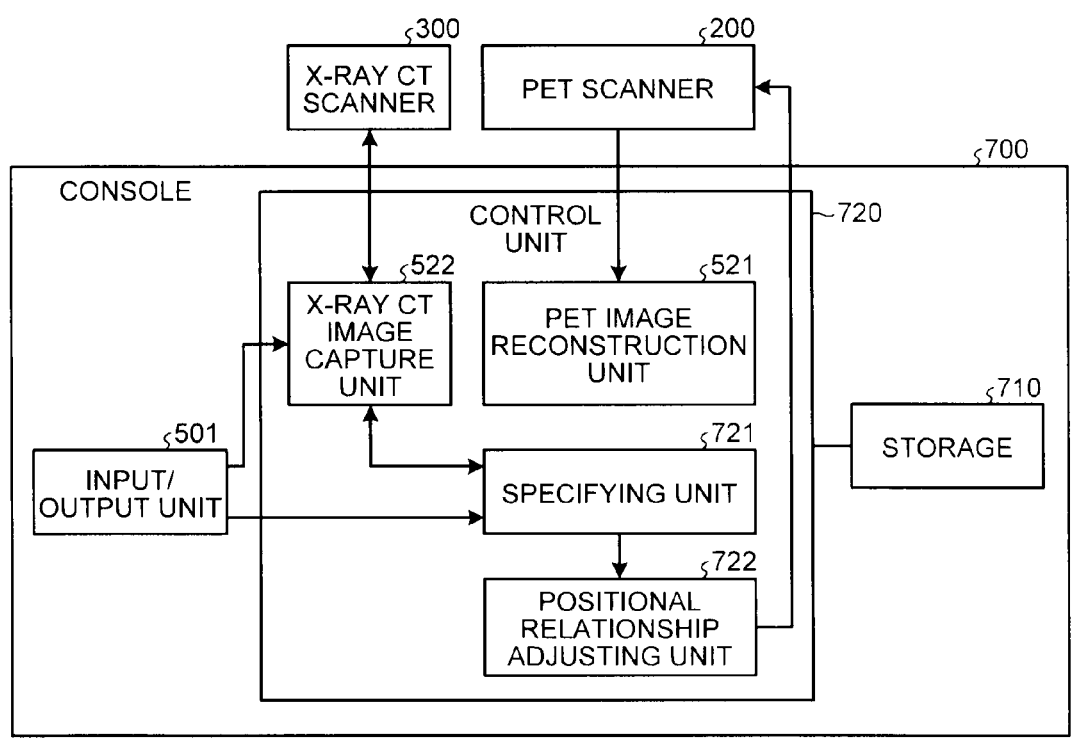
FIG. 14 is a block diagram of an example of the structure of a console without the previous image table.

For example, the radiographic apparatus may adjust the positional relationship between the detector and the examinee without using the previous image table 511. FIG. 14 is a block diagram illustrating an example of the structure of a console without using the previous image table. The same components as those in the console according to the first embodiment shown in FIG. 8 are denoted by the same reference numerals and a description thereof will be repeated.

For convenience of explanation, FIG. 14 shows the PET scanner 200 and the X-ray CT scanner 300 in addition to a console 700. In the example shown in FIG. 14, the console 700 includes the input/output unit 501, storage 710, and a control unit 720. The storage 710 is connected to the control unit 720. The storage 710 stores data used in various kinds of processes of the control unit 720.

The control unit 720 is connected to the input/output unit 501 and the storage 710. The control unit 720 includes an internal memory that stores programs for defining various kinds of procedures and controls various kinds of processes. The control unit 720 corresponds to an electronic circuit, such as an ASIC, an FPGA, a CPU, and an MPU. In the example shown in FIG. 14, the control unit 720 includes the PET image reconstruction unit 521, the X-ray CT image capture unit 522, a specifying unit 721, and a positional relationship adjusting unit 722.

The specifying unit 721 specifies the position of the region of interest in the captured shape image. For example, when receiving a specification operation of specifying the position of the region of interest from the user, the specifying unit 721 specifies the position of the region of interest.

This will be described in detail. The X-ray CT image capture unit 522 captures a scanoscope image or an X-ray CT image. The specifying unit 721 outputs the scanoscope image or the X-ray CT image captured by the X-ray CT image capture unit 522 to the user through the input/output unit 501 and receives a specification operation of specifying a position in the output scanoscope image or X-ray CT image from the user through the input/output unit 501. Then, the specifying unit 721 specifies the position specified by the specification operation received from the user as the position of the region of interest.

For example, the specifying unit 721 may store specification information for specifying positions in the captured shape image in advance and may specify the position of the region of interest in the captured shape image on the basis of the specification information. In this case, the specifying unit 721 stores the name of a part of the examinee, such as the "head," the "ear," or the "heart," as the specification information. Then, the specifying unit 721 specifies the position of the part indicated by the specification information from the captured shape image. For example, the specification information is input by the user in advance.

The positional relationship adjusting unit 722 adjusts the positional relationship between the examinee and the detector 210 that detects radiation for generating a nuclear medicine image on the basis of the position in the captured shape image that is specified by the specifying unit 721.

Figure 15:
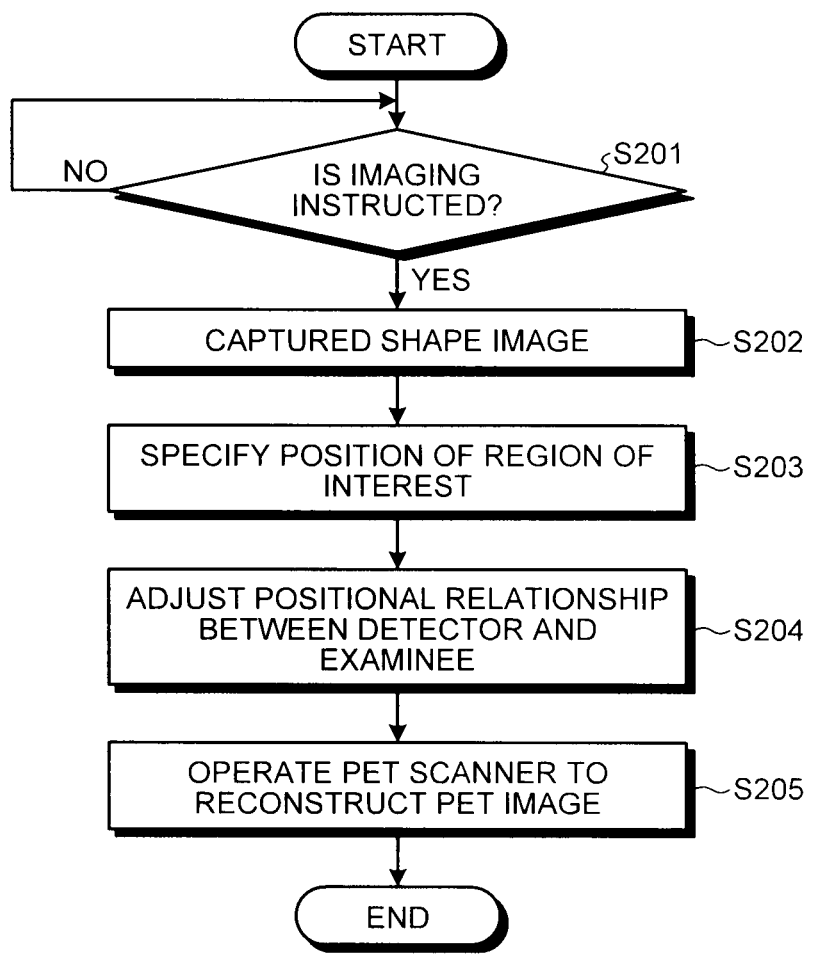
FIG. 15 is a flowchart of an example of the flow of a process when the previous image table is not used.

FIG. 15 is a flowchart illustrating an example of the flow of the process when the previous image table is not used.

As shown in FIG. 15, when an imaging instruction is received (Step S201: Yes), the X-ray CT image capture unit 522 operates the X-ray CT scanner 300 to capture an X-ray CT image (Step S202). That is, the X-ray CT image capture unit 522 captures a captured shape image. For example, the X-ray CT image capture unit 522 captures the scanoscope image of the examinee.

Then, the specifying unit 721 specifies the position of the region of interest in the captured shape image (Step S203). For example, when receiving a position in the scanoscope image from the user, the specifying unit 721 specifies the position of the region of interest.

Then, the positional relationship adjusting unit 722 adjusts the positional relationship between the detector 210 and the examinee on the basis of the position in the captured shape image which is specified by the specifying unit 721 (Step S204). For example, the positional relationship adjusting unit 722 adjusts the positional relationship between the detector 210 and the examinee such that the position of the region of interest specified by the specifying unit 721 is the center of the effective field of view of the PET scanner 200.

Then, the PET image reconstruction unit 521 operates the PET scanner 200 to reconstruct a PET image (Step S205).

As described above, in the method that does not use the previous image table, it is possible to improve the image quality of the region of interest to be more than that of other regions without using the previous image table. For example, the method that does not use the previous image table is effective in a case in which the area of the detector is large or a case in which a position is roughly specified on the basis of the captured shape image and then a dynamic imaging operation is performed.

Among the processes in the above-mentioned embodiment, some or all of the processes that are automatically performed may be manually performed, or some or all of the processes that are manually performed may be automatically performed by a known method. In addition, information including the process sequence, the control sequence, the detailed names, and various kinds of data or parameters described in the specification or the drawings (FIGS. 1 to 15) may be arbitrarily changed except for special cases.

The drawings show the function and concept of the components of each apparatus, but the components of each apparatus are not necessarily physically configured as shown in the drawings. That is, the examples of the separation or integration of the apparatuses are not limited to those shown in the drawings, but some or all of the apparatuses may be functionally or physically separated or integrated in any unit according to various kinds of loads or use conditions. For example, in the above-described embodiment, the console 500 reconstructs the PET image or the X-ray CT image and performs determination on the basis of the number of time radiation is detected. However, the embodiment is not limited thereto. For example, a control unit that reconstructs the PET image may be provided separately from the console 500. In this case, the control unit that reconstructs the PET image may be provided outside the PET-CT apparatus 100 and may be connected to the PET-CT apparatus 100 through a network.

A control program of the PET-CT apparatus 100 according to the above-described embodiment may be distributed through a network, such as the Internet. In addition, the control program may be stored in a computer-readable recording medium, such as a hard disk, a flexible disk (FD), a CD-ROM, an MO, or a DVD, may be read from the recording medium by a computer, and may be executed.

While certain embodiments have been described, these embodiments have been presented by way of example only, and are not intended to limit the scope of the embodiments. Indeed, the novel radiographic apparatuses, control methods, and computer program products described herein may be embodied in a variety of other forms; furthermore, various omissions, substitutions and changes in the form of the radiographic apparatuses, control methods, and computer program products described herein may be made without departing from the spirit of the embodiments. The accompanying claims and their equivalents are intended to cover such forms or modifications as would fall within the scope and spirits of the embodiments.

According to a radiographic apparatus of at least one embodiment described above, the radiographic apparatus includes a positional relationship adjusting unit that adjusts the positional relationship between the examinee and a detector that detects radiation for generating a nuclear medicine image, on the basis of the position in the captured shape image which is specified by the specifying unit. As a result, it is possible to improve the detection efficiency of a pair of radiations emitted from the positron emitting nuclide in the region of interest to be more than that a pair of radiations emitted from the positron emitting nuclide in other regions and improve image quality in the region of interest to be more than that in other regions.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiographic apparatus, comprising:
   a storage configured to store a previously obtained shape image of an examinee in association with a functional image that was captured in association with the previously obtained shape image;
   a shape image capture unit configured to capture a current shape image of the examinee;
   an image acquiring unit configured to acquire the previously obtained shape image of the examinee from the storage;
   a position acquiring unit configured to acquire, from the storage, the functional image, specify a region of interest in the acquired functional image, and acquire, in the previously obtained shape image, a first position corresponding to the specified region of interest;
   a conversion unit configured to convert the first position in the previously obtained shape image into a second position in the captured shape image, on the basis of a correspondence between the second position in the captured shape image and the first position in the previously obtained shape image; and
   a positional relationship adjusting unit configured to adjust a positional relationship between the examinee and a detector which detects radiation for generating a nuclear medicine image, on the basis of the second position in the captured shape image, which is a conversion result of the conversion unit.

2. The radiographic apparatus according to claim 1, wherein the positional relationship adjusting unit is configured to adjust the positional relationship such that the second position, which is the conversion result of the conversion unit, is a center of an effective field of view of the detector.

3. The radiographic apparatus according to claim 2, wherein, when the position acquiring unit is configured to acquire a plurality of positions, the positional relationship adjusting unit calculates a center of the plurality of positions and adjusts the positional relationship such that the position of the calculated center is the center of the effective field of view of the detector.

4. The radiographic apparatus according to claim 2, wherein, when the position acquiring unit is configured to acquire a plurality of positions, the positional relationship adjusting unit adjusts the positional relationship such that one of the plurality of positions which is selected by an operator is the center of the effective field of view of the detector.

5. A control method, comprising:

capturing a current shape image of an examinee;

acquiring, from a storage a previously obtained shape image of the examinee, which is stored in the storage in association with a functional image that was captured in association with the previously obtained shape image;

acquiring, from the storage, the functional image, specifying a region of interest in the acquired functional image, and acquiring, in the previously obtained shape image, a first position corresponding to the specified region of interest;

converting the first position in the previously obtained shape image into a second position in the captured shape image, on the basis of a correspondence between the second position in the captured shape image and the first position in the previously obtained shape image; and adjusting a positional relationship between the examinee and a detector which detects radiation for generating a nuclear medicine image, on the basis of the second position in the captured shape image, which is the conversion result.

6. A non-transitory computer readable medium comprising instructions that cause a computer to execute:

capturing a current shape image of an examinee;

acquiring, from a storage, a previously obtained shape image of the examinee, which is stored in the storage in association with a functional image that was captured in association with the previously obtained shape image;

acquiring, from the storage, the functional image, specifying a region of interest in the acquired functional image, and acquiring, in the previously obtained shape image, a first position corresponding to the specified region of interest;

converting the first position in the previously obtained shape image into a second position in the captured shape image, on the basis of a correspondence between the second position in the captured shape image and the first position in the previously obtained shape image; and adjusting a positional relationship between the examinee and a detector which detects radiation for generating a nuclear medicine image, on the basis of the second position in the captured shape image, which is a conversion result.

* * * * *